(12) United States Patent
Guederian et al.

(10) Patent No.: US 7,204,854 B2
(45) Date of Patent: Apr. 17, 2007

(54) METAL BACK PROSTHETIC GLENOID COMPONENT WITH CEMENTED PEGS AND HOLLOW METAL CAGE SCREW

(75) Inventors: Gregory Guederian, Naples, FL (US); Peter Habermeyer, Stuttgart (DE)

(73) Assignee: Arthrex, Inc., Naples, FL (US)

( * ) Notice: Subject to any disclaimer, the term of this patent is extended or adjusted under 35 U.S.C. 154(b) by 236 days.

(21) Appl. No.: 10/639,520

(22) Filed: Aug. 13, 2003

(65) Prior Publication Data
US 2004/0059424 A1 Mar. 25, 2004

Related U.S. Application Data

(60) Provisional application No. 60/403,429, filed on Aug. 15, 2002.

(51) Int. Cl.
*A61F 2/40* (2006.01)
(52) U.S. Cl. ..................... 623/19.11; 623/908
(58) Field of Classification Search ............. 623/17.11, 623/17.16, 19.11, 19.13, 908; 606/73
See application file for complete search history.

(56) References Cited

U.S. PATENT DOCUMENTS

| | | | |
|---|---|---|---|
| 4,653,487 A * | 3/1987 | Maale | 606/62 |
| 4,964,865 A | 10/1990 | Burkhead et al. | |
| 4,986,833 A | 1/1991 | Worland | |
| 5,032,132 A | 7/1991 | Matsen, III et al. | |
| 5,080,673 A | 1/1992 | Burkhead et al. | |
| 5,084,050 A * | 1/1992 | Draenert | 606/73 |
| 5,593,448 A | 1/1997 | Dong | |
| 5,702,447 A | 12/1997 | Walch et al. | |
| 5,702,453 A * | 12/1997 | Rabbe et al. | 623/17.16 |
| 5,800,551 A | 9/1998 | Williamson et al. | |
| 6,120,503 A * | 9/2000 | Michelson | 606/61 |
| 6,156,069 A * | 12/2000 | Amstutz | 623/22.11 |
| 6,228,119 B1 | 5/2001 | Ondrla et al. | |
| 6,306,170 B2 * | 10/2001 | Ray | 606/61 |
| 6,569,186 B1 * | 5/2003 | Winters et al. | 606/73 |

FOREIGN PATENT DOCUMENTS

EP 538 895 A2 4/1993

* cited by examiner

*Primary Examiner*—Brian E. Pellegrino
(74) *Attorney, Agent, or Firm*—Dickstein Shapiro LLP

(57) ABSTRACT

A prosthetic glenoid component for attachment to a glenoid surface of a scapula to replace a natural socket of a shoulder and to provide a bearing surface for a head portion of an arm bone or humerus. The glenoid component has a metal back with integrally formed attachment legs which are cemented into corresponding holes formed in the glenoid surface, and also has an opening for receiving a hollow metal cage which is screwed into the glenoid surface.

4 Claims, 3 Drawing Sheets

US 7,204,854 B2

METAL BACK PROSTHETIC GLENOID COMPONENT WITH CEMENTED PEGS AND HOLLOW METAL CAGE SCREW

This application claims the benefit of U.S. Provisional Application No. 60/403,429, filed Aug. 15, 2002.

FIELD OF THE INVENTION

The present invention relates to the field of prosthetic devices and, in particular, to a prosthetic glenoid component for attachment to a glenoid surface of a scapula to replace a natural socket of a shoulder and to provide a bearing surface for a head portion of an arm bone or humerus.

BACKGROUND OF THE INVENTION

It is known in the prior art to provide glenoid components for replacing a glenoid surface which have a two piece construction and comprise plastic inserts which slide into or are otherwise coupled to metal backings. The metal backings are used to secure the plastic inserts to the glenoid surface. The backings are typically made from titanium or other suitable metals, and are typically attached to the glenoid surface using metal fixation screws or cages, such as disclosed in U.S. Pat. No. 4,865,605 and EP 0 538 895 A2. Other glenoid components known in the art use a plurality of attachment pegs for penetrating the glenoid to secure the glenoid to the glenoid surface. See, e.g., U.S. Pat. No. 5,080,673.

There is needed, therefore, a new glenoid prosthesis device and a method of affixing the glenoid prosthesis device to a resected surface of a scapula more securely than provided in the prior art.

SUMMARY OF THE INVENTION

The present invention provides a prosthetic glenoid component which attaches to a glenoid surface of a scapula to replace a natural socket of a shoulder and provides a bearing surface for a head portion of an arm bone or humerus. More particularly, the present invention provides a metal back glenoid component having integrally formed attachment legs which are cemented into corresponding holes formed in the glenoid surface, and also having an opening for receiving a hollow, threaded cage which is screwed into the glenoid surface.

BRIEF DESCRIPTION OF THE DRAWINGS

These and other features and advantages of the invention will be better understood from the following detailed description, which is provided in connection with the accompanying drawings.

DETAILED DESCRIPTION OF THE INVENTION

In the following detailed description, reference is made to various specific embodiments of the invention. These embodiments are described with sufficient detail to enable those skilled in the art to practice the invention. It is to be understood that other embodiments may be employed, and that various structural, logical and electrical changes may be made without departing from the spirit or scope of the invention.

The invention will now be described with reference to FIGS. 1–4 illustrating a metal back glenoid constructed in accordance with the invention.

The glenoid component 2 of the present invention is designed for use in a total shoulder replacement procedure. In a total shoulder replacement procedure, a humeral component having a head portion is used to replace the natural head portion of the humerus. The humeral component typically has an elongated intramedullary stem to secure the humeral component to the humerus. The glenoid portion of the scapula is resurfaced with a glenoid component which provides a bearing surface for the head portion of the humeral component. For instance, the glenoid prosthesis 2 can be positioned in a resected portion of the head of the scapula.

Figure 1:
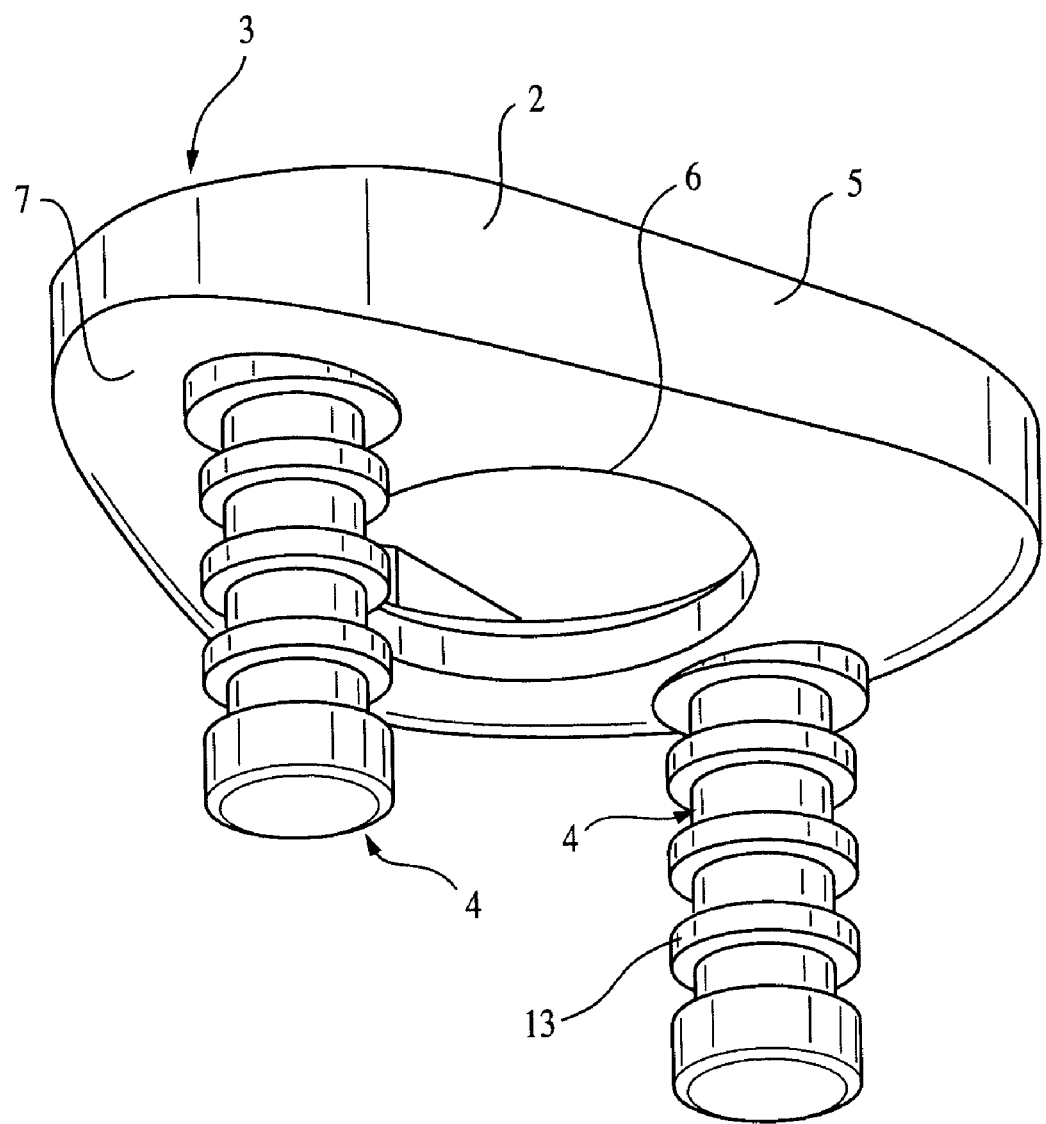
FIG. 1 is a close-up view of a glenoid prosthesis comprising pegs constructed in accordance with an embodiment of the present invention.

Referring now to FIG. 1, the glenoid prosthesis 2 used is preferably a metal back glenoid prosthesis 2. The metal back glenoid prosthesis 2 preferably comprises titanium metal. The metal back glenoid prosthesis 2 consists of a lateral surface 3, flat sidewalls 5, a substantially flat medial surface 7, and at least two pegs 4 extending medially from the flat medial surface 7. The glenoid prosthesis 2 is formed to be approximately the same shape as a natural glenoid cavity.

The lateral articulating surface 3 of the glenoid prosthesis 2 provides a bearing surface for the head portion of the humeral component. In a preferred embodiment, an insert 12 can be provided that slides into grooves on the lateral articulating surface 3 to form a substantially spherical contact from which the head portion of the humeral component will rest against.

The glenoid prosthesis 2 is attached to the resected portion of the scapula. Portions of the scapula are resected such that a relatively flat surface is provided to which the glenoid prosthesis 2 will become affixed to. The amount of scapula that is resected will depend upon the thickness of the metal back glenoid prosthesis 2. After a flat surface on the scapula has been obtained, at least two holes are drilled substantially perpendicular into the resected portion to provide cylindrical sidewalls and a flat end. Typically, the holes are drilled to be larger than the pegs 4 in order to allow cement to be provided therein, if desired. In a preferred embodiment, cement is provided into the provided peg holes and applied on the resected surface of the scapula.

The pegs 4 are then inserted into the peg holes and the medial surface 7 is positioned adjacent to the resected surface of the scapula. The cement then provides a continuous bond between the medial surface 7 and the resected surface of the scapula, and between the pegs 4 and peg holes formed in the scapula. The affixation of the medial surface 7 to the resected portion of the scapula prevents movement of the glenoid prosthesis 2 and the bone. The presence of cement enhances the affixation of the glenoid prosthesis 2 to the resected surface of the scapula.

In a preferred embodiment, the pegs 4 are provided with a plurality of circumferential grooves 13 that are disposed throughout the length of the pegs 4. The circumferential grooves 13 increase the surface area of the pegs 4 to which cement can bond to. In essence, a stronger bond is achieved to which the pegs 4 can be strongly affixed within the peg holes of the scapula in which cement is provided therein.

As a result, the metal back glenoid component 2 of the present invention provides a unique combination of attachment means including a plurality of pegs 4 which are designed to be inserted and cemented into predrilled holes in the resected surface of the scapula. Metal back glenoid component 2 also includes a central aperture 6 for receiving a hollow metal cage screw 8 which is formed of titanium and can optionally be provided with fenestrations 10 (FIG. 2) to promote bone growth. Metal cage screw 8 is received in a cavity formed by a coring reamer (not shown), and provides the primary fixation for the glenoid component, while pegs 4 provide additional fixation and prevent rotation. The lateral medial surface 7 of the glenoid prosthesis can also be cemented to the glenoid surface to provide even further adhesion.

Figure 2:
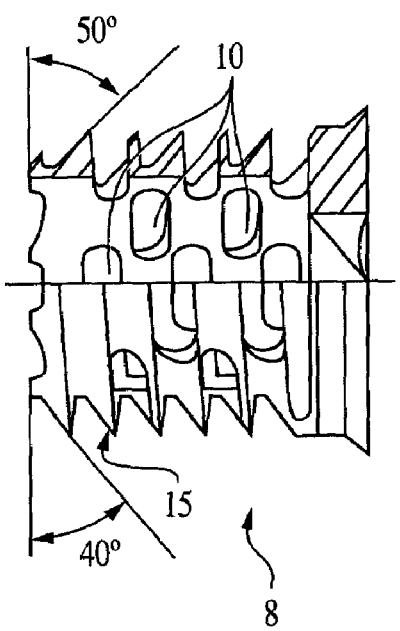
FIG. 2 is a side sectional view of an exemplary metal cage screw that is used in conjunction with the glenoid prosthesis of FIG. 1 constructed in accordance with an embodiment of the present invention.

FIG. 2 is a side-sectional view of metal cage screw 8. As illustrated, a plurality of fenestrations 10 may extend through the cylindrically-shaped, hollow cage screw 8. As the bone grows, it can grow through the fenestrations 10, thus providing adhesion properties in addition to those provided above. For exemplary purposes, metal cage screw 8 is illustrated with a plurality of fenestrations 10 offset from each other.

Figure 3:
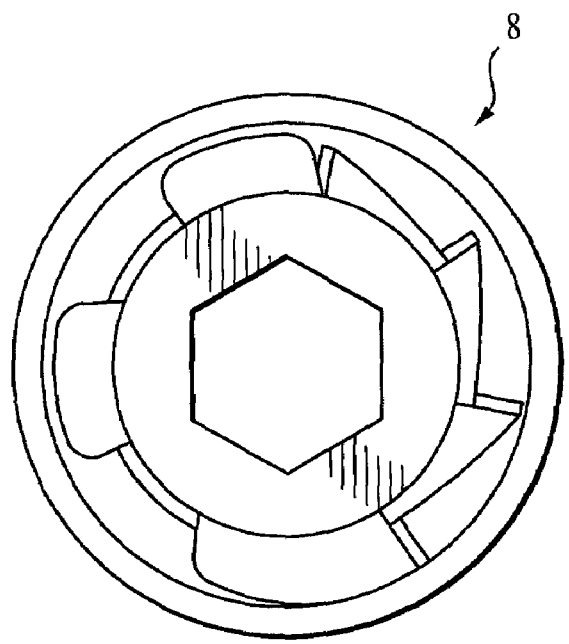
FIG. 3 is a top-side view of the exemplary metal cage screw of FIG. 2.

The metal cage screw 8 is provided with circumferential threads 15 as illustrated in FIG. 2. The circumferential threads 15 are provided at an angle that ranges from about 40° to about 50° on the main shaft of the metal cage screw 8. FIG. 3 is a top-down view of metal cage screw 8.

Figure 4:
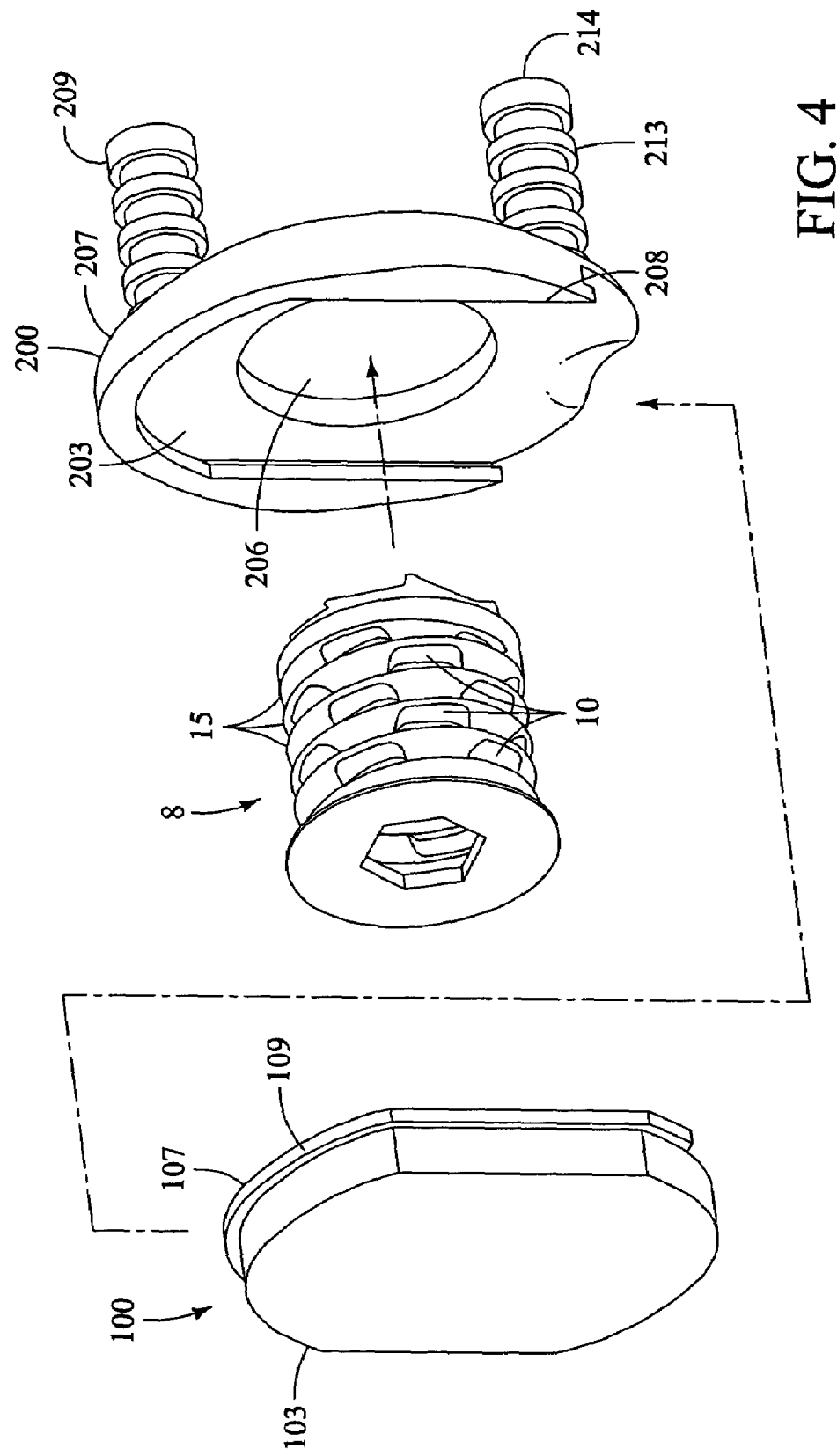
FIG. 4 is an assembly drawing of a glenoid prosthesis and an insert constructed in accordance with the present invention.

Referring now to FIG. 4, an assembly drawing of the invention is shown in which glenoid prosthesis 200 with metal cage screw 8 is shown with a polyethylene insert 100, which provides a smooth bearing surface on the medial side of the prosthesis. Insert 100 has tapered edges 208 which slide into the indented raised edges 108 of the glenoid prosthesis 200 to couple the insert to the prosthesis.

The above description and drawings are only to be considered illustrative of exemplary embodiments which achieve the features and advantages of the invention. Although exemplary embodiments of the present invention have been described and illustrated herein, many modifications, even substitutions of materials, can be made without departing from the spirit or scope of the invention. Accordingly, the above description and accompanying drawings are only illustrative of exemplary embodiments that can achieve the features and advantages of the present invention. It is not intended that the invention be limited to the embodiments shown and described in detail herein. The invention is limited only by the scope of the appended claims.

What is claimed as new and desired to be protected by Letters Patent of the United States is:

1. A method of attaching a glenoid prosthesis, comprising:
    resecting a portion of the glenoid cavity on the surface of a scapula to provide a resected scapula surface;
    drilling at least two holes substantially perpendicular to the resected scapula surface;
    filling the holes with cement;
    providing a metallic glenoid prosthesis comprising at least two pegs and a central aperture;
    inserting the at least two pegs of the glenoid prosthesis in the drilled holes filled with cement, the pegs each having a plurality of circumferential grooves disposed around the full circumference of the pegs; and
    advancing a hollow metal cage screw with fenestrations and circumferential threads through the central aperture of the glenoid prosthesis and into a hole in the scapula to affix the glenoid prosthesis to the resected scapula surface.

2. The method of claim 1, wherein the holes are formed by drilling.

3. The method of claim 1, further comprising the step of forming a cylindrical hole in the scapula for receiving the hollow metal cage screw.

4. The method of claim 3, wherein the cylindrical hole is formed with a coring reamer.

* * * * *